(12) United States Patent
Drzewinski et al.

(10) Patent No.: US 7,205,271 B2
(45) Date of Patent: Apr. 17, 2007

(54) RHEOLOGY MODIFIER/HAIR STYLING RESIN

(75) Inventors: Michael Drzewinski, Long Valley, NJ (US); Joseph Albanese, Hillsborough, NJ (US); Eduardo T. Yap, Franklin Lakes, NJ (US); Jenn S. Shih, Paramus, NJ (US)

(73) Assignee: ISP Investments Inc., Wilmington, DE (US)

( * ) Notice: Subject to any disclaimer, the term of this patent is extended or adjusted under 35 U.S.C. 154(b) by 247 days.

(21) Appl. No.: 10/964,948

(22) Filed: Oct. 14, 2004

(65) Prior Publication Data
US 2006/0084586 A1  Apr. 20, 2006

(51) Int. Cl.
*C11D 3/37* (2006.01)
*A61K 8/00* (2006.01)
*A61K 8/72* (2006.01)

(52) U.S. Cl. .............. 510/475; 510/119; 510/121; 510/130; 424/401; 424/70.11; 424/70.15; 424/70.16

(58) Field of Classification Search ............... 510/119, 510/121, 130, 475; 424/401, 70.11, 70.15, 424/70.16
See application file for complete search history.

(56) References Cited

U.S. PATENT DOCUMENTS 6,361,768 B1 * 3/2002 Galleguillos et al. .... 424/70.12

* cited by examiner

*Primary Examiner*—Brian Mruk
(74) *Attorney, Agent, or Firm*—William J. Davis; Walter Katz

(57) ABSTRACT

A rheology modifier/hair styling resin which is a crosslinked, linear poly(vinyl amide/polymerizable carboxylic acid) copolymer exhibits advantageous hair care properties of high viscosity and long-lasting curl retention.

22 Claims, 2 Drawing Sheets

Viscosity vs. pH for Resin of Invention (Ex. 1)
Brookfield RVT, T-bar C @ 10 RPM, 60 sec, 1% solids

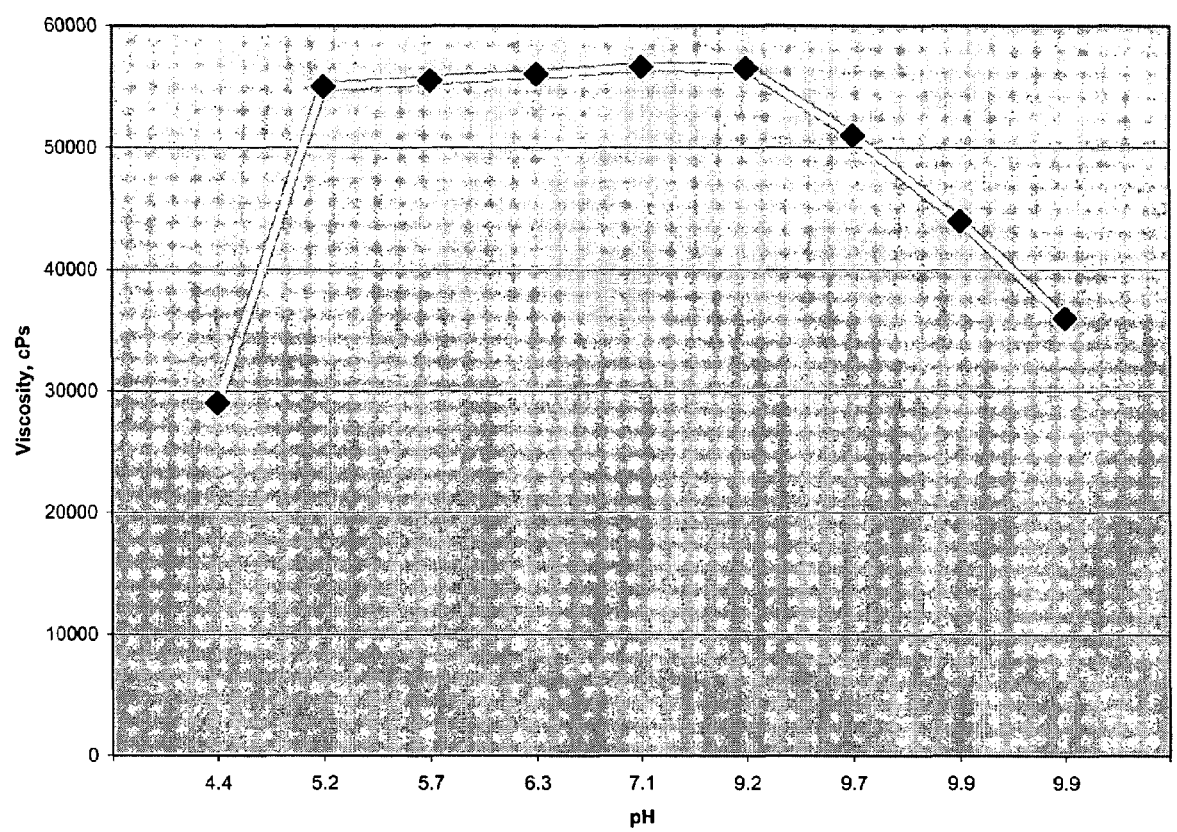
Figure 1. Viscosity vs. pH for Resin of Invention (Ex. 1)
Brookfield RVT, T-bar C @ 10 RPM, 60 sec, 1% solids

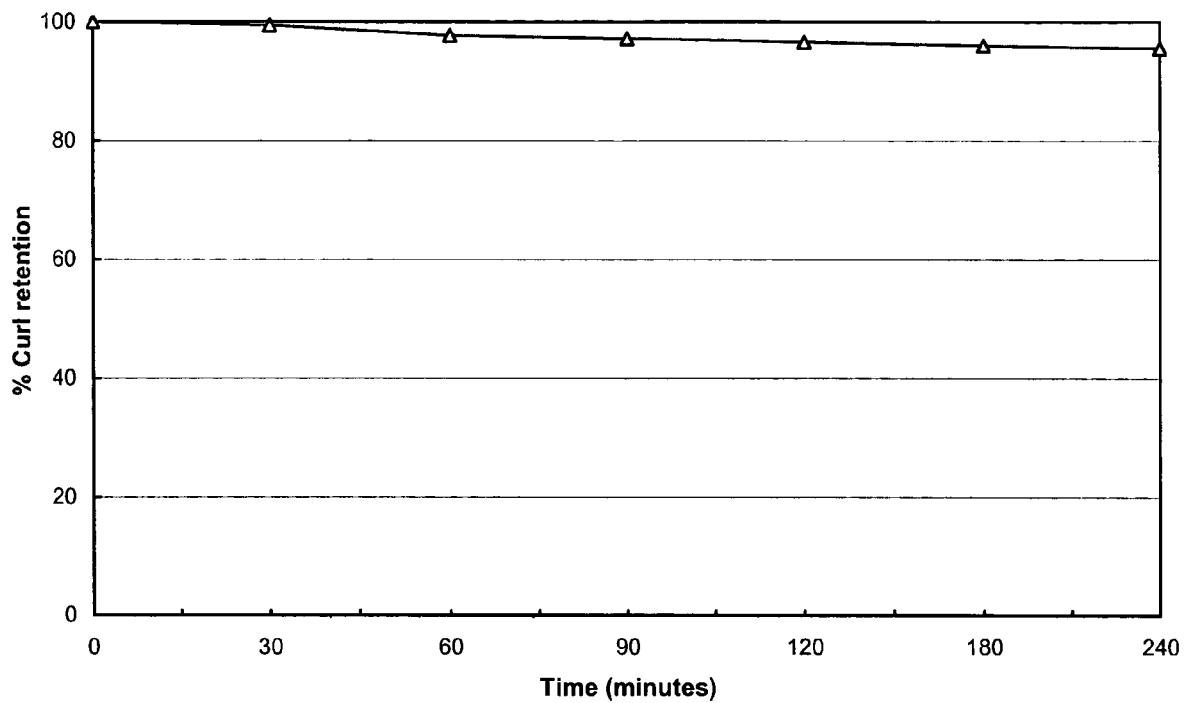
Figure 2. Curl retention vs. Time for Hair care formulation of Ex. 1.

RHEOLOGY MODIFIER/HAIR STYLING RESIN

BACKGROUND OF THE INVENTION

1. Field of the Invention

This invention relates to hair care compositions, and, more particularly, to a rheology modifier/hair styling resin which is a crosslinked, linear poly(vinyl amide/polymerizable carboxylic acid) copolymer for use in such compositions.

2. Description of the Prior Art

J. Shih, in U.S. Pat. No. 5,015,708, described a process for making terpolymers of vinyl pyrrolidone, acrylic acid and lauryl methacrylate monomers by precipitation polymerization in an aliphatic hydrocarbon solvent.

Frenz, V. in WO 02/32975, Apr. 25, 2002, described absorbent materials made by grafting acrylic acid monomer onto polyvinyl pyrrolidone polymer in water in the presence of a crosslinking agent. The resultant crosslinked graft copolymer matrix contained 79.9–99.9% of acrylic acid.

Accordingly, it is an object of this invention to provide a rheology modifier/hair styling resin which is a crosslinked, linear poly(vinyl amide/polymerizable carboxylic acid) copolymer; and a process for making same.

Another object herein is to provide a crosslinked, linear copolymer which is particularly advantageous for use in hair care compositions.

Still another object is to provide hair care formulations which exhibits both high viscosity and long-lasting curl retention for the user.

SUMMARY OF THE INVENTION

What is described herein is a rheology modifier/hair styling resin which is a crosslinked, linear poly(vinyl amide/polymerizable carboxylic acid) copolymer.

Suitable vinyl amides include vinyl pyrrolidone, vinyl caprolactam, N-vinyl formamide, N-vinylacetamide, N-vinyl-N-methylacetamide and mixtures thereof, preferably vinyl pyrrolidone.

Suitable polymerizable carboxylic acids include (meth) acrylic acid, crotonic acid, itaconic acid, maleic acid and mixtures thereof, preferably acrylic acid.

Suitable crosslinkers have at least two free radical polymerizable groups in the molecule, e.g. pentaerythritol triallylether, pentaerythritol triacrylate, pentaerythritol tetraacrylate or methylene bisacrylamide.

The composition of the rheology modifier/hair styling resin of the present invention includes a vinyl amide, in an amount of by weight, 1–99% of the composition, a polymerizable carboxylic acid in an amount of 1–99% of the composition, and a crosslinker in an amount of 0.2–3%, based on total weight of monomers.

Preferably, the vinyl amide monomer is present in an amount of 25–80%, the polymerizable carboxylic acid in an amount of 20–80%, and the crosslinker 0.4–2%, based on total weight of monomers.

Optionally, the rheology modifier/hair styling resin may include one or more additional monomers, e.g. lauryl (meth) acrylate, stearyl (meth)acrylate, alkyl (meth)acrylamide or alkyl (meth)acrylate. The alkyl can be $C_1$ to $C_{30}$ or polyethylene oxide.

As another feature of the invention, there is described a process of making the rheology modifier/hair styling resin which comprises precipitation polymerizing, by wt., 5–50%, preferably 10–25%, of a mixture of a vinyl amide, a polymerizable carboxylic acid and a crosslinker, in the presence of 50–95%, preferably 75–90%, of a non-polar, removable organic solvent, and 0.1–5%, preferably 0.5–2%, of a free radical initiator, based on total weight of monomers.

Yet another feature of the invention is the provision of a personal care composition, e.g. a hair care composition, which includes the rheology modifier/hair styling resin of the invention, suitably in an amount of 0.1–20% by wt. of the composition, preferably 0.2–10%, and most preferably 0.5–5%.

Typical hair care compositions which include the invention resin have an advantageously high viscosity of about 30,000 to 100,000 cps, preferably 40,000 to 70,000 cps, at a pH of about 5 to 9 and a long-lasting curl retention of 95 to 100% over a 4-hour period at 90% RH and 80° F.

The hair care compositions of the invention also exhibit other advantageous user properties, such as shine, stiffness, crunch, stiffness after $5^{th}$ and $10^{th}$ compression, curl snap, comb drag, residue on comb, manageability, hair feel and static.

IN THE DRAWINGS

FIG. 1 is a plot of Viscosity vs pH for the rheology modifier/hair styling resin of the present invention.

FIG. 2 is a plot of Curl Retention vs Time for a hair care formulation which includes the resin of the invention.

DETAILED DESCRIPTION OF THE INVENTION

The scope of the invention is illustrated by the following Table:

TABLE

RHEOLOGY MODIFIER/HAIR STYLING RESIN OF INVENTION

| Monomer | Example | Suitable Compositional Range | Preferred Compositional Range |
|---|---|---|---|
| Vinyl amide | Vinyl Pyrrolidone, Vinyl Caprolactam, N-vinyl-formamide, N-vinyl acetamide, N-vinyl-N-methyl acetamide | 1–99% | 20–80% |
| Polymerizable carboxylic acid | (Meth)acrylic acid, crotonic acid, itaconic acid, maleic acid | 1–99% | 20–80% |
| Crosslinker, more than two free radical | Pentaerythritol triallylether, methylene bisacrylamide, | 0.2–3% based on total weight | 0.4–2 |

TABLE-continued

RHEOLOGY MODIFIER/HAIR STYLING RESIN OF INVENTION

| polymerizable groups in the molecule | Pentaerythritol triacrylate, Pentaerythritol tetraacrylate | of monomers | |
|---|---|---|---|
| Optional monomers | Lauryl (meth)acrylate, stearyl (meth)acrylate, alkyl (meth)acrylamide, alkyl(meth)acrylate | | |
| Free radical initiator, e.g. peroxide, perester, percarbonate, Vazo | t-Butylperoxy pivalate, 2,2'-azobis(2-methylbutane-nitrile) | 0.1–5%, based on total monomer weight | 0.5–2% |
| Volatile non-polar organic solvent or mixed solvents | Heptane, benzene, isopropyl acetate, cyclohexane | 95–50% (solvent) 5–50% (polymer) | 85–75% 15–25% |

| Process Conditions | Suitable Range | Preferred Range |
|---|---|---|
| Polymerization temperature | 40° C.–150° C. | 55° C.–100° C. |
| Monomer feeding time, hrs (2 feeding lines) | 0–10 | 3–5 |

The process of making the rheology modifier/hair styling resin of the present invention is suitably carried out in a non-polar solvent, e.g. heptane, benzene, isopropyl acetate or cyclohexane, which can be removed easily after the polymerization, in the presence of a free radical initiator, at a polymerization temperature of 40°–150° C., preferably 55°–100° C., at monomer feeding times in 2 feeding lines of 0–10 hrs, preferably 3–5 hrs. The reactants are monomers and crosslinker. The product is a crosslinked, linear copolymer of a vinyl amide, e.g. vinyl pyrrolidone, and a polymerizable carboxylic acid, e.g. acrylic acid, which is crosslinked with a suitable crosslinking agent e.g. pentaerythritol triallyl ether in the form of a powder.

FIG. 1 is a graph of viscosity vs. pH for a solution of fixative resin of the invention at a 1% solids level in water. As shown, the viscosity of the solution is a desirably high value of about 55,000 cps at a pH of about 5–9. FIG. 2 shows the advantageous effective curl retention property of the resin for a typical hair care formulation which includes the resin of Example 1. Typically, a 95–100% curl retention is achieved for such formulation even after 4 hours.

Aqueous solutions of the resin of the invention also have the advantageous property of a high yield stress in dynes/cm$^2$, generally 10 to 100,000, and preferably 100 to 10,000.

Examples of the process are shown in the examples which follow.

EXAMPLE 1

Crosslinked, Linear Poly(N-Vinyl Pyrrolidone) (VP)/Acrylic Acid (AA) Copolymer Crosslinked with Pentaerythritol Triallyl Ether (PETE Into a 1-liter, four-necked glass kettle, equipped with two feeding pumps, an anchor agitator, a thermocouple and a condenser, 500 g of heptane as solvent was charged and agitated at 200 rpm while being purged with nitrogen throughout the process. The solvent then was heated to 65° C. with an oil bath and held there for 30 minutes. Feeding Solution I was prepared by mixing 50 g of N-vinylpyrrolidone (VP) and 1.0 g of pentaerythritol triallylether (PETE). Feeding Solution 11 was prepared by weighing 50 g of acrylic acid (AA) into a bottle. 200 microliter of Luperox® 11M75 as initiator was charged into the kettle. Then Feeding Solutions I and II were simultaneously pumped into the kettle over a period of 4 hours at a constant feeding rate. The resulting solution then was held at 65° C. for 1 hour and the reaction temperature was raised to 90° C. Then an additional 100 microliter of Luperox® 11M75 was added every two hours for 4 times and the reactor was held at 90° C. for two additional hours after the last dose of Luperox® 11 M75 was charged. The contents then were cooled and discharged. The solvent was removed at an oven temperature of 100° C. The resultant resin powder was further dried in a vacuum oven at 100° C. The product was a crosslinked, linear copolymer of VP and AA crosslinked with PETE in a wt. ratio of 50/50/1.

EXAMPLES 2–10

| Example | VP (g) | AA (g) | PETE (g) |
|---|---|---|---|
| 2 | 75 | 25 | 0.5 |
| 3 | 50 | 50 | 0.5 |
| 4 | 25 | 75 | 0.5 |
| 5 | 75 | 25 | 1.0 |
| 6 | 50 | 50 | 2.0 |
| 7 | 25 | 75 | 1.0 |
| 8 | 75 | 25 | 1.5 |
| 9 | 50 | 50 | 1.5 |
| 10 | 25 | 75 | 1.5 |

EXAMPLE 11

Crosslinked, Linear Poly(N-Vinyl Caprolactam) (VCL)/Acrylic Acid) Copolymer Crosslinked with Pentaerythritol Triallyl Ether Into a 1-liter, four-necked glass kettle, equipped with an anchor agitator, a thermocouple and a condenser, 500 g of heptane as solvent was charged and agitated at 200 rpm while being purged with nitrogen throughout the process. The solvent was heated to 65° C. with an oil bath and held there for 30 minutes. Feeding Solution I was prepared by mixing 50 g of N-vinylcaprolactam (VCL) and 1.5 g of pentaerythritol triallylether (PETE). Feeding solution II was prepared by weighing 50 g of acrylic acid (M) into a bottle.

Then 200 microliter of t-butyl peroxypivalate initiator was charged into the kettle. The Feeding Solution I and Feeding Solution II were simultaneously charged into the kettle over 4 hours at a constant feeding rate. The solution was held at 65° C. for 1 hour and the temperature was raised to 90° C. Then an additional 200 microliter of t-butyl peroxypivalate was added every two hours for 4 times and the reactor was held at 90° C. for two additional hours after the last dose of t-butyl peroxypivalate was charged. The contents then were cooled and discharged. The solvent was removed at an oven temperature of 100° C. The resultant resin powder was further dried in a vacuum oven at 100° C. The product was a crosslinked, linear copolymer of VCL and M crosslinked with PETE in a wt. ratio of 50/50/1.5.

EXAMPLE 11A

Crosslinked, Linear Poly(N-Vinyl Pyrrolidone) (VP)/Acrylic Acid (AA)/Stearyl Methacrylate (SM) Terpolymer Crosslinked with Pentaerythritol Trialyl Ether (PETE)

Into a 1-liter, four-necked glass kettle, equipped with two feeding pumps, an anchor agitator, a thermocouple and a condenser, 500 g of heptane as solvent was charged and agitated at 200 rpm while being purged with nitrogen throughout the process. The solvent then was heated to 65° C. with an oil bath and held there for 30 minutes. Feeding Solution I was prepared by mixing 60 g of N-vinylpyrrolidone (VP), 15 g of stearyl methacrylate (SM) and 1.0 g of pentaerythritol triallylether (PETE). Feeding Solution II was prepared by weighing 25 g of acrylic acid (M) into a bottle. 200 microliter of Luperox® 11M75 as initiator was charged into the kettle. Then Feeding Solutions I and II were simultaneously pumped into the kettle over a period of 4 hours at a constant feeding rate. The resulting solution then was held at 65° C. for 1 hour and the reaction temperature was raised to 90° C. Then an additional 100 microliter of Luperox® 11M75 was added every two hours for 4 times and the reactor was held at 90° C. for two additional hours after the last dose of Luperox® 11M75 was charged. The contents then were cooled and discharged. The solvent was removed at an oven temperature of 100° C. The resultant resin powder was further dried in a vacuum oven at 100° C. The product was a crosslinked, linear terpolymer of VP, M and SM crosslinked with PETE in a wt. ratio of 600/25/15/1.

EXAMPLES 12–14

| Example | VCL (g) | AA (g) | PETE (g) |
|---------|---------|--------|----------|
| 12 | 75 | 25 | 1.5 |
| 13 | 25 | 75 | 1.5 |
| 14 | 50 | 50 | 2.0 |

EXAMPLE 15

Crosslinked, Linear Poly(N-Vinyl Pyrrolidone)/Methacrylic Acid (MAA) Copolymer Crosslinked with Pentaerythritol Triallyl Ether Into a 1-liter, four-necked glass kettle, equipped with two feeding pumps, an anchor agitator, a thermocouple and a condenser, 600 g of heptane as solvent is charged and agitated at 300 rpm while being purged with nitrogen throughout the process. The solvent then is heated to 70° C. with an oil bath and held there for 30 minutes. Feeding Solution I is prepared by mixing 50 g of N-vinylpyrrolidone (VP) and 1.0 g of pentaerythritol triallylether (PETE). Feeding solution II is prepared by weighing 50 g of methacrylic acid (MAA) into a bottle. Then 300 microliter of t-butyl peroxypivalate initiator is charged into the kettle.

The Feeding Solution I and Feeding Solution II are simultaneously pumped into the kettle over 5 hours at a constant feeding rate. The solution is held at 70° C. for 1 hour and the solution is transferred to stainless high pressure reactor. Then an additional 0.5 g of di-t-butylperoxide is added. The temperature of the reactor is raised to 130° C. and held for 10 hours. The contents then are cooled and discharged. The solvent is removed at an oven temperature of 100° C. The resultant resin powder is further dried in a vacuum oven at 100° C. The product is a crosslinked, linear copolymer of VP and MM crosslinked with PETE in a wt. ratio of 50/50/1.

Representative personal care formulations which include the resin of the invention are shown below.

EXAMPLE 16

| Hair Styling Gel Composition | |
|---|---|
| Ingredient | Wt. % |
| DI water | 98.51 |
| AMP-95 (Aminomethylpropanol 95%) | 0.49 |
| Polymer of Example 1 | 1.00 |
| | 100% |

Procedure:
1. Charge 93.51 parts of DI water into a suitable vessel.
2. Add 0.05 parts of pre-neutralizer 2-amino-2-methylpropanol (AMP).
3. Start agitation at medium speed.
4. Slowly sprinkle in 1.0 parts of the polymer powder. Alternatively the powder can be "dumped" it will eventually disperse throughout on its own.
5. Allow to mix for 30–60 minutes, at medium-low speed, to ensure complete dispersion, if white particles are present, continue mixing until particles have disappeared. The mix time should be doubled is the polymer was "dumped."
6. Pre-mix 0.44 parts of neutralizer AMP with 5 parts of DI water, and add to the main batch.
7. Lower the RPM's to avoid excessive aeration.
8. Mix for 30–60 minutes to ensure uniform gel.
9. Product should appear as clear gel, pH 6.7, and viscosity RV TC@ 10 rpm 50,000 cPs.

EXAMPLE 16A

| Hair Styling Gel Composition | |
|---|---|
| Ingredient | Wt. % |
| DI water | 98.35 |
| AMP-95 (Aminomethylpropanol 95%) | 0.65 |

-continued

Hair Styling Gel Composition

| Ingredient | Wt. % |
|---|---|
| Polymer of Example 1 | 0.50 |
| Carbomer 980 | 0.50 |
| | 100% |

EXAMPLE 16B

Hair Styling Gel Composition

| Ingredient | Wt. % |
|---|---|
| DI water | 97.95 |
| AMP-95 (Aminomethylpropanol 95%) | 0.55 |
| Polymer of Example 1 | 0.50 |
| Aculyn 22 | 1.00 |
| | 100% |

EXAMPLE 16C

Hair Fixative Composition

| Ingredient | Wt. % |
|---|---|
| DI water | 98.51 |
| AMP-95 (Aminomethylpropanol 95%) | 0.49 |
| Polymer of Example 1 | 1.00 |
| | 100% |

EXAMPLE 17

Clear Bath Gel Composition

| Ingredient | Wt. % |
|---|---|
| Water | 42.07 |
| AMP-95 | 0.93 |
| Polymer of Example 1 | 2.00 |
| Sodium Laureth Sulfate (28%) | 40.00 |
| Cocamidopropyl betaine (35%) | 15.00 |
| | 100% |

EXAMPLE 18

Antibacterial Liquid Hand Soap

| Ingredient | Wt. % |
|---|---|
| Water | 54.57 |
| AMP-95 | 0.49 |

-continued

Antibacterial Liquid Hand Soap

| Ingredient | Wt. % |
|---|---|
| Polymer of Example 1 | 1.00 |
| Ammonium Lauryl Sulfate (30%) | 25.00 |
| Disodium Laureth Sulfosuccinate (40%) | 8.00 |
| Cocamidopropyl betaine (35%) | 4.00 |
| Glycerin | 2.00 |
| Propylene Glycol | 2.00 |
| Triclosan | 0.50 |
| Parfum | 1.29 |
| Polysorbate-20 | 0.50 |
| Liquid Germall ® Plus | 0.15 |
| Dimethicone (and) Gelatin (and) Gum Acacia (and) Xanthan Gum | 0.50 |
| | 100% |

EXAMPLE 19

Clear Shampoo Gel

| Ingredient | Wt. % |
|---|---|
| Water | 40.82 |
| AMP-95 | 0.93 |
| Polymer of Example 1 | 2.00 |
| Sodium Laureth Sulfate (28%) | 40.00 |
| Cocamidopropyl betaine (35%) | 15.00 |
| Polyquaternium-11 (Gafquat ® 755N) | 0.10 |
| Propylene Glycol (and) Diazolidinyl Urea (and) Iodopropynyl Butylcarbamate (Liquid Germall ® Plus) | 0.15 |
| Hallcrest blue beads (Shea butter) | 0.50 |
| Hallcrest pink beads (Dimethicone) | 0.50 |
| | 100% |

EXAMPLE 20

Complex Conditioning Shampoo

| Ingredient | INCI name | Wt. % |
|---|---|---|
| Water | DI water | 52.77 |
| AMP-95 | Amonomethyl Propanol (95%) | 0.49 |
| Polymer of Example 1 | Crosslinked VP/AA | 1.00 |
| Stepanol WAT-K | TEA Lauryl Sulfate (39.23% actives) | 30.56 |
| Si-tech GF 3092 | Cyclopentasiloxane (and) Dimethiconol | 1.00 |
| Ninol CMP | Cocamide MEA | 3.00 |
| Maprosyl 30 | Sodium Lauroyl Sarcosinate (30% actives) | 1.26 |
| Dissolvene NA2-S | Disodium EDTA | 3.33 |
| Soy Tein NL | Hydrolyzed Soy Protein | 0.10 |
| Cerasynt IP | Glycol Stearate (and) Other Ingredients | 1.25 |
| Orchid complex | Caprylic/Capric Triglyceride (and) Cymbidium Grandiflorum Flower Extract | 1.50 |
| Conditioneze NT 20 | Polyquaternium-28 (19.4% actives) | 1.30 |

-continued

Complex Conditioning Shampoo

| Ingredient | INCI name | Wt. % |
|---|---|---|
| Parfum | Fragrance | 1.29 |
| Tween-20 | Polysorbate-20 | 0.50 |
| Liquid Germall Plus | Propylene Glycol (and) Diazolidinyl Urea (and) Iodopropynyl Butylcarbamate | 0.15 |
| Hallcrest Pink Beads | Dimethicone (and) Gelatin (and) Gum Acacia (and) Xanthan Gum | 0.50 |
| | | 100% |

EXAMPLE 21

Hair Fixative Composition

| Ingredient | Wt. % |
|---|---|
| Water | 96.51 |
| AMP-95 | 0.49 |
| Polymer of Example 1 | 1.00 |
| Omnirez 2000 (50%) | 2.00 |
| | 100% |

EXAMPLE 22

Hair Fixative Composition

| Ingredient | Wt. % |
|---|---|
| Water | 79.81 |
| AMP-95 | 0.49 |
| Polymer of Example 1 | 1.00 |
| Gaffix VC 713 copolymer (37%) | 3.70 |
| Advantage S (10%) | 10.00 |
| Copolymer 845 (20%) | 5.00 |
| | 100% |

EXAMPLE 23

Hair Fixative Composition

| Ingredient | Wt. % |
|---|---|
| Water | 78.51 |
| AMP-95 | 0.49 |
| Polymer of Example 1 | 1.00 |
| Gafquat 755 (20%) | 5.00 |
| Advantage S (10%) | 10.00 |
| Copolymer 845 (20%) | 5.00 |
| | 100% |

EXAMPLE 24

Hair Fixative Composition

| Ingredient | Wt. % |
|---|---|
| Water | 79.81 |
| AMP-95 | 0.49 |
| Polymer of Example 1 | 1.00 |
| Ganex P 904 LC (10%) | 3.70 |
| Advantage S (10%) | 10.00 |
| Copolymer 845 (20%) | 5.00 |
| | 100% |

EXAMPLE 25

Hair Fixative Composition

| Ingredient | Wt. % |
|---|---|
| Water | 95.17 |
| AMP-95 | 0.49 |
| Polymer of Example 1 | 1.00 |
| Gafquat 440 (30%) | 3.34 |
| | 100% |

EXAMPLE 26

Hair Fixative Composition

| Ingredient | Wt. % |
|---|---|
| Water | 93.51 |
| AMP-95 | 0.49 |
| Polymer of Example 1 | 1.00 |
| Copolymer 845 (20%) | 5.00 |
| | 100% |

EXAMPLE 27

Hair Care Product

| Ingredient | Wt. % |
|---|---|
| Water | 93.51 |
| AMP-95 | 0.49 |
| Polymer of Example 1 | 1.00 |
| Styleze W-20 (20% sol'n) | 5.00 |
| | 100% |

EXAMPLE 28

Hair Care Product

| Ingredient | Wt. % |
|---|---|
| Water | 88.41 |
| AMP-95 | 0.49 |
| Polymer of Example 1 | 1.00 |
| Styleze CC-10 | 10.00 |
|  | 100% |

EXAMPLE 29

Hair Care Composition

| Ingredient | Wt. % |
|---|---|
| Water | 88.51 |
| AMP-95 | 0.49 |
| Polymer of Example 1 | 1.00 |
| Ganex P904LC (10%) | 10.00 |
|  | 100% |

EXAMPLE 30

Personal Care Product

| Ingredient | Wt. % |
|---|---|
| Water | 93.51 |
| AMP-95 | 0.49 |
| Polymer of Example 1 | 1.00 |
| Conditioneze 7 (10%) | 10.00 |
|  | 100% |

EXAMPLE 31

Personal Care Composition

| Ingredient | Wt. % |
|---|---|
| Water | 95.17 |
| AMP-95 | 0.49 |
| Polymer of Example 1 | 1.00 |
| Aquaflex XL-30 (30%) | 3.34 |
|  | 100% |

EXAMPLE 32

Personal Care Composition

| Ingredient | Wt. % |
|---|---|
| Water | 93.51 |
| AMP-95 | 0.49 |
| Polymer of Example 1 | 1.00 |
| Gafquat 755 (20%) | 5.00 |
|  | 100% |

EXAMPLE 33

Personal Care Composition

| Ingredient | Wt. % |
|---|---|
| Water | 93.51 |
| AMP-95 | 0.49 |
| Polymer of Example 1 | 1.00 |
| Gafquat HS-100 (20%) | 5.00 |
|  | 100% |

EXAMPLE 34

Personal Care Composition

| Ingredient | Wt. % |
|---|---|
| Water | 93.51 |
| AMP-95 | 0.49 |
| Polymer of Example 1 | 1.00 |
| Gafquat 755N (20%) | 5.00 |
|  | 100% |

EXAMPLE 35

Personal Care Composition

| Ingredient | Wt. % |
|---|---|
| Water | 94.81 |
| AMP-95 | 0.49 |
| Polymer of Example 1 | 1.00 |
| Gaffix VC 713 copolymer (37%) | 3.70 |
|  | 100% |

EXAMPLE 36

Personal Care Composition

| Ingredient | Wt. % |
| --- | --- |
| Water | 95.18 |
| AMP-95 | 0.49 |
| Polymer of Example 1 | 1.00 |
| PVP K-30 (30%) | 3.33 |
| | 100% |

EXAMPLE 37

Personal Care Composition

| Ingredient | Wt. % |
| --- | --- |
| Water | 88.51 |
| AMP-95 | 0.49 |
| Polymer of Example 1 | 1.00 |
| Advantage S (10% sol'n) | 10.00 |
| | 100% |

EXAMPLE 38

Night Cream Composition

| Phase | Ingredient | % w/w |
| --- | --- | --- |
| A | Water | 70.60 |
| | Na2EDTA | 0.05 |
| | Polymer of Example 1 | 1.00 |
| | Propylene glycol | 1.00 |
| B | Ceraphyl 847 | 5.00 |
| | Si-Tec DM 1000 | 2.00 |
| | Ceraphyl 494 | 4.70 |
| | Si-Tec PTM 200 (phenyl trimeticone) | 2.00 |
| | Si-Tec DMC 3071 | 2.50 |
| | Si-Tec CM 040 | 2.50 |
| C | NaOH (10%) | 1.50 |
| D | dl-alpha-tocopheryl acetate | 0.30 |
| | Actiphyte of Licorice Root BG50P | 0.50 |
| | Gluadin W-20 | 0.50 |
| | Sheer Musk (71110M) | 0.30 |
| | Liquid Germall Plus | 0.50 |
| E | Escalol 577 (Benzophenone-4) | 0.05 |
| | Water | 5.00 |
| | | 100% |

Procedure:
1. Combine ingredients in phase A with mixing.
2. Combine phase B. Mix until uniform.
3. Add phase B to phase A with mixing.
4. Add phase C.
5. Add ingredients in phase D.
6. Combine phase E. Mix until clear.
7. Add phase E with mixing.

EXAMPLE 39

Night Cream Composition

| Phase | Ingredient | % w/w |
| --- | --- | --- |
| A | Water | 70.60 |
| | Na2EDTA | 0.05 |
| | Polymer of Example 1 | 1.00 |
| | Propylene glycol | 1.00 |
| B | Ceraphyl 847 | 5.00 |
| | Si-Tec DM 1000 | 2.00 |
| | Ceraphyl 494 | 4.60 |
| | Si-Tec PTM 200 (phenyl trimeticone) | 2.00 |
| | Si-Tec CM 040 | 2.50 |
| C | NaOH (10%) | 2.00 |
| | DI water | 1.10 |
| D | dl-alpha-tocopheryl acetate | 0.30 |
| | Actiphyte of Licorice Root BG50P | 0.50 |
| | Gluadin W-20 | 0.50 |
| | Sheer Musk (71110M) | 0.30 |
| | Liquid Germall Plus | 0.50 |
| E | Escalol 577 (Benzophenone-4) | 0.05 |
| | Water | 5.00 |
| | | 100% |

Procedure:
1. Combine ingredients in phase A with mixing.
2. Combine phase B. Mix until uniform.
3. Add phase B to phase A with mixing.
4. Add phase C.
5. Add ingredients in phase D.
6. Combine phase E. Mix until clear.
7. Add phase E with mixing.

EXAMPLE 40

Sunscreen Lotion

| Phase | Ingredient | % w/w |
| --- | --- | --- |
| A | DI water | 76.65 |
| | Versene NA | 0.05 |
| | Propylene glycol | 1.00 |
| | Polymer of Example 1 | 1.00 |
| B | Escalol 557 | 7.00 |
| | Escalol 567 | 2.00 |
| | Escalol 587 | 3.00 |
| | Ceraphyl 45 | 4.00 |
| | Polysorbate-20 | 0.50 |
| C | NaOH (50% w/w) | 0.20 |
| | DI water | 3.30 |
| D | Sheer Musk | 0.30 |
| | Germaben II-E | 1.00 |
| | | 100% |

Procedure:
1. Disperse phase A ingredient into water with stirring.
2. Combine first five phase B ingredients. Stir until uniform.
3. Add phase B to phase A with homogenizing @ RT. Stir until uniform.
4. When uniform, add phase C.
5. Add phase D ingredient with stirring. QS for water loss

EXAMPLE 41

Sunscreen Lotion

| Phase | Ingredient | % w/w |
|---|---|---|
| A | DI water | 76.65 |
|  | Versene NA | 0.05 |
|  | Propylene glycol | 1.00 |
|  | Polymer of Example 1 | 1.00 |
| B | Escalol 557 | 7.00 |
|  | Escalol 567 | 2.00 |
|  | Escalol 587 | 3.00 |
|  | Ceraphyl 45 | 4.00 |
|  | Si-Tec 3071 | 1.00 |
| C | NaOH (50% w/w) | 0.20 |
|  | DI water | 2.80 |
| D | Sheer Musk | 0.30 |
|  | Germaben II-E | 1.00 |
|  |  | 100% |

Procedure:
1. Disperse phase A ingredient into water with stirring.
2. Combine first five phase B ingredients. Stir until uniform.
3. Add phase B to phase A with homogenizing @ RT. Stir until uniform.
4. When uniform, add phase C.
5. Add phase D ingredient with stirring. QS for water loss

EXAMPLE 42

Day Cream

| Phase | Ingredient | % w/w |
|---|---|---|
| A | DI water | 69.80 |
|  | EDTA (di-sodium) | 0.10 |
|  | Glycerin | 1.00 |
|  | Polymer of Example 1 | 1.00 |
|  | Propylene glycol | 1.00 |
| B | Ceraphyl 230 | 4.00 |
|  | Ceraphyl 494 | 6.00 |
|  | Ceraphyl 368 | 10.00 |
|  | Prolipid 151 | 3.00 |
| C | NaOH (50% w/w) | 0.20 |
|  | DI water | 2.80 |
| D | Sheer Musk | 0.50 |
|  | Liquid Germall Plus | 0.60 |
|  |  | 100% |

Procedure:
1. Add ingredients in phase A to water with stirring. Heat to 65° C.
2. Combine phase B. Heat with stirring until P-151 dissolve.
3. Add phase B to phase A with homogenizing.
4. When uniform, add phase C with homogenizing. Cool to 35° C.
5. Add phase D with stirring. QS for water loss While the resin of the invention is particularly useful for hair care, it will be understood that it can be used in other personal care applications, such as skin care or as an absorbent material in appropriate applications such as diapers, etc.

FIG. 1 herein shows the viscosity vs. pH property of the fixative resin of the invention t 1% solids in water. The viscosity is a desirably high value of about 55,000 cps at a pH of about 5–9. FIG. 2 herein shows the advantageous effective curl retention vs. time for a typical hair care formulation of the invention which includes the resin of Example 1. Substantially 95–100% curl retention is achieved even after 4 hours.

Any known conditioning agent is useful in the hair compositions of this invention. Conditioning agents function to improve the cosmetic properties of the hair, particularly softness, thickening, untangling, feel, and static electricity and may be in liquid, semi-solid, or solid form such as oils, waxes, or gums. Similarly, any known skin altering agent is useful in the compositions of this invention. Preferred conditioning agents include cationic polymers, cationic surfactants and cationic silicones.

Conditioning agents may be chosen from synthesis oils, mineral oils, vegetable oils, fluorinated or perfluorinated oils, natural or synthetic waxes, silicones, cationic polymers, proteins and hydrolyzed proteins, ceramide type compounds, cationic surfactants, fatty amines, fatty acids and their derivatives, as well as mixtures of these different compounds.

The synthesis oils include polyolefins, e.g., poly-α-olefins such as polybutenes, polyisobutenes and polydecenes. The polyolefins can be hydrogenated.

The mineral oils suitable for use in the compositions of the invention include hexadecane and oil of paraffin.

Suitable animal and vegetable oils include sunflower, corn, soy, avocado, jojoba, squash, raisin seed, sesame seed, walnut oils, fish oils, glycerol tricaprocaprylate, Purcellin oil or liquid jojoba.

Suitable natural or synthetic oils include eucalyptus, lavender, vetiver, litsea cubeba, lemon, sandalwood, rosemary, chamomile, savory, nutmeg, cinnamon, hyssop, caraway, orange, geranium, cade, and bergamot.

Suitable natural and synthetic waxes include carnauba wax, candelila wax, alfa wax, paraffin wax, ozokerite wax, vegetable waxes such as olive wax, rice wax, hydrogenated jojoba wax, absolute flower waxes such as black currant flower wax, animal waxes such as bees wax, modified bees wax (cerabellina), marine waxes and polyolefin waxes such as polyethylene wax.

The cationic polymers (other than the poly (alkyl) vinyllactam polymers according to the invention) that may be used as a conditioning agent according to the invention are those known to improve the cosmetic properties of hair treated by detergent compositions. The expression "cationic polymer" as used herein, indicates any polymer containing cationic groups and/or ionizable groups in cationic groups. The cationic polymers used generally have a molecular weight the average number of which falls between about 500 and 5,000,000 and preferably between 1000 and 3,000,000.

The preferred cationic polymers are chosen from among those containing units including primary, secondary, tertiary, and/or quaternary amine groups that may either form part of the main polymer chain or a side chain.

Useful cationic polymers include known polyamine, polyaminoamide, and quaternary polyammonium types of polymers, such as:

(1) homopolymers and copolymers derived from acrylic or methacrylic esters or amides. The copolymers can contain one or more units derived from acrylamides, methacrylamides, diacetone acrylamides, acrylamides and methacrylamides, acrylic or methacrylic acids or their esters, vinyllactams such as vinyl pyrrolidone or vinyl caprolactam, and vinyl esters. Specific examples include: copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone/dialkylaminoalkyl acrylate or methacrylate, optionally quaternized, such as the products sold under the name GAFQUAT by International Specialty Products; the dimethyl amino ethyl methacrylate/vinyl caprolactam/vinyl pyrrolidone terpolymers, such as the product sold under the name GAFFIX VC 713 by International Specialty Products; the vinyl pyrrolidone/methacrylamidopropyl dimethylamine copolymer, marketed under the name STYLEZE CC 10 by International Specialty Products; and the vinyl pyrrolidone/quaternized dimethyl amino propyl methacrylamide copolymers such as the product sold under the name GAFQUAT HS 100 by International Specialty Products.

(2) derivatives of cellulose ethers containing quaternary ammonium groups, such as hydroxy ethyl cellulose quaternary ammonium that has reacted with an epoxide substituted by a trimethyl ammonium group.

(3) derivatives of cationic cellulose such as cellulose copolymers or derivatives of cellulose grafted with a hydrosoluble quaternary ammonium monomer, as described in U.S. Pat. No. 4,131,576, such as the hydroxy alkyl cellulose, and the hydroxymethyl-, hydroxyethyl- or hydroxypropyl-cellulose grafted with a salt of methacryloyl ethyl trimethyl ammonium, methacrylamidopropyl trimethyl ammonium, or dimethyl diallyl ammonium.

(4) cationic polysaccharides such as described in U.S. Pat. Nos. 3,589,578 and 4,031,307, guar gums containing cationic trialkyl ammonium groups and guar gums modified by a salt, e.g., chloride of 2,3-epoxy propyl trimethyl ammonium.

(5) polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers.

(6) water-soluble polyamino amides prepared by polycondensation of an acid compound with a polyamine. These polyamino amides may be reticulated.

(7) derivatives of polyamino amides resulting from the condensation of polyalcoylene polyamines with polycarboxylic acids followed by alcoylation by bi-functional agents.

(8) polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers are described in U.S. Pat. Nos. 3,227,615 and 2,961,347.

(9) the cyclopolymers of alkyl dialyl amine or dialkyl diallyl ammonium such as the homopolymer of dimethyl diallyl ammonium chloride and copolymers of diallyl dimethyl ammonium chloride and acrylamide.

(10) quaternary diammonium polymers such as hexadimethrine chloride. Polymers of this type are described particularly in U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945, and 4,027,020.

(11) quaternary polyammonium polymers, including, for example, Mirapol® A 15, Mirapol®AD1, Mirapol®AZ1, and Mirapol® 175 products sold by Miranol.

(12) the quaternary polymers of vinyl pyrrolidone and vinyl imidazole such as the products sold under the names Luviquat® FC 905, FC 550, and FC 370 by BASF.

(13) quaternary polyamines.

(14) reticulated polymers known in the art.

Other cationic polymers that may be used within the context of the invention are cationic proteins or hydrolyzed cationic proteins, polyalkyleneimines such as polyethyleneimines, polymers containing vinyl pyridine or vinyl pyridinium units, condensates of polyamines and epichlorhydrins, quaternary polyurethanes, and derivatives of chitin.

Preferred cationic polymers are derivatives of quaternary cellulose ethers, the homopolymers and copolymers of dimethyl diallyl ammonium chloride, quaternary polymers of vinyl pyrrolidone and vinyl imidazole, and mixtures thereof.

The conditioning agent can be any silicone known by those skilled in the art to be useful as a conditioning agent. The silicones suitable for use according to the invention include polyorganosiloxanes that are insoluble in the composition. The silicones may be present in the form of oils, waxes, resins, or gums. They may be volatile or non-volatile. The silicones can be selected from polyalkyl siloxanes, polyaryl siloxanes, polyalkyl aryl siloxanes, silicone gums and resins, and polyorgano siloxanes modified by organofunctional groups, and mixtures thereof.

Suitable polyalkyl siloxanes include polydimethyl siloxanes with terminal trimethyl silyl groups or terminal dimethyl silanol groups (dimethiconol) and polyalkyl ($C_1$–$C_{20}$) siloxanes.

Suitable polyalkyl aryl siloxanes include polydimethyl methyl phenyl siloxanes and polydimethyl diphenyl siloxanes, linear or branched.

The silicone gums suitable for use herein include polydiorganosiloxanes preferably having a number-average molecular weight between 200,000 and 1,000,000, used alone or mixed with a solvent. Examples include polymethyl siloxane, polydimethyl siloxane/methyl vinyl siloxane gums, polydimethyl siloxane/diphenyl siloxane, polydimethyl siloxane/phenyl methyl siloxane and polydimethyl siloxane/diphenyl siloxane/methyl vinyl siloxane.

Suitable silicone resins include silicones with a dimethyl/trimethyl siloxane structure and resins of the trimethyl siloxysilicate type.

The organo-modified silicones suitable for use in the invention include silicones such as those previously defined and containing one or more organofunctional groups attached by means of a hydrocarbon radical and grafted siliconated polymers. Particularly preferred are amino functional silicones.

The silicones may be used in the form of emulsions, nano-emulsions, or micro-emulsions.

The conditioning agent can be a protein or hydrolyzed cationic or non-cationic protein. Examples of these compounds include hydrolyzed collagens having triethyl ammonium groups, hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having groups of quaternary ammonium on the polypeptide chain, including at least one $C_1$–$C_{18}$ alkyl.

Hydrolyzed proteins include Croquat L, in which the quaternary ammonium groups include a $C_{12}$ alkyl group, Croquat M, in which the quaternary ammonium groups include $C_{10}$–$C_{18}$ alkyl groups, Croquat S in which the quaternary ammonium groups include a $C_{18}$ alkyl group and Crotein Q in which the quaternary ammonium groups include at least one $C_1$–$C_{18}$ alkyl group. These products are sold by Croda.

The conditioning agent can comprise quaternized vegetable proteins such as wheat, corn, or soy proteins such as cocodimonium hydrolyzed wheat protein, laurdimonium hydrolyzed wheat protein and steardimonium hydrolyzed wheat protein.

According to the invention, the conditioning agent can be a ceramide type of compound such as a ceramide, a glycoceramide, a pseudoceramide, or a neoceramide. These compounds can be natural or synthetic. Compounds of the ceramide type are, for example, described in Patents pending DE4424530, DE4424533, DE4402929, DE4420736, WO95/23807, WO94/07844, EP-A-0646572, WO95/16665, FR-2 673 179, EP-A-0227994, WO 94/07844, WO 94/24097, and WO 94/10131. Ceramide type compounds useful herein include 2-N-linoleoyl amino-octadecane-1,3-diol, 2-N-oleoyl amino-octadecane-1,3-diol, 2-N-palmitoyl amino-octadecane-1,3-diol, 2-N-stearoyl amino-octadecane-1,3-diol, 2-N-behenoyl amino-octadecane-1,3-diol, 2-N-[2-hydroxy-palmitoyl]-amino-octadecane-1,3-diol, 2-N-stearoyl amino-octadecane-1,3,4-triol, N-stearoyl phytosphingosine, 2-N-palmitoyl amino-hexadecane-1,3-diol, bis-(N-hydroxy ethyl N-cetyl) malonamide, N(2-hydroxy ethyl)-N-(3-cetoxyl-2-hydroxy propyl) amide of cetylic acid, N-docosanoyl N-methyl-D-glucamine and mixtures of such compounds.

The conditioning agent can be a cationic surfactant such as a salt of a primary, secondary, or tertiary fatty amine, optionally polyoxyalkylenated, a quaternary ammonium salt, a derivative of imadazoline, or an amine oxide. Suitable examples include mono-, di-, or tri-alkyl quaternary ammonium compounds with a counterion such as a chloride, methosulfate, tosylate, etc. including, but not limited to, cetrimonium chloride, dicetyldimonium chloride, behentrimonium methosulfate, and the like. The presence of a quaternary ammonium compound in conjunction with the polymer described above reduces static and enhances combing of hair in the dry state. The polymer also enhances the deposition of the quaternary ammonium compound onto the hair substrate thus enhancing the conditioning effect of hair.

The conditioning agent can be any fatty amine known to be useful as a conditioning agent; e.g. dodecyl, cetyl or stearyl amines, such as stearamidopropyl dimethylamine.

The conditioning agent can be a fatty acid or derivatives thereof known to be useful as conditioning agents. Suitable fatty acids include myristic acid, palmitic acid, stearic acid, behenic acid, oleic acid, linoleic acid, and isostearic acid. The derivatives of fatty acids include carboxylic ester acids including mono-, di-, tri- and tetra-carboxylic acids.

The conditioning agent can be a fluorinated or perfluorinated oil. Fluorinated oils include perfluoropolyethers described in EP-A-486135 and the fluorohydrocarbon compounds described in WO 93/11103. The fluoridated oils may also be fluorocarbons such as fluoramines, e.g., perfluorotributylamine, fluoridated hydrocarbons, such as perfluorodecahydronaphthalene, fluoroesters, and fluoroethers.

Of course, mixtures of two or more conditioning agents can be used.

The conditioning agent or agents can be present in an amount of 0.001% to 20%, preferably from 0.01% to 10%, and even more preferably from 0.1% to 3% by weight based on the total weight of the final composition.

The composition of the invention can contain one or more protecting agents to prevent or limit the degrading effects of natural physical and/or chemical assaults on the keratinous materials.

The protecting agent can be chosen from hydrosoluble, liposoluble and water-insoluble UV filters, antiradical agents, antioxidants, vitamins and pro-vitamins. The above-described cationic polymer enhances the deposition of these materials onto the hair or skin substrate enhancing protection of hair to UV damage.

Organic UV filters (systems that filter out UV rays) can be chosen from among hydrosoluble or liposoluble filters, whether siliconated or nonsiliconated, and mineral oxide particles, the surface of which may be treated.

Hydrosoluble organic UV filters may be chosen from para-amino benzoic acid and its salts, anthranilic acid and its salts, salicylic acid and its salts, hydroxy cinnamic acid and its salts, sulfonic derivatives of benzothiazoles, benzimidizoles, benzoxazoles and their salts, sulfonic derivatives of benzophenone and their salts, sulfonic derivatives of benzylidene camphor and their salts, derivatives of benzylidene camphor substituted by a quaternary amine and their salts, derivatives of phthalydene-camphosulfonic acids and their salts, sulfonic derivatives of benzotriazole, and mixtures thereof.

Hydrophilic polymers which have light-protective qualities against UV rays can be used. These include polymers containing benzylidene camphor and/or benzotriazole groups.

Suitable liposoluble organic UV filters include derivatives of para-aminobenzoic acid, such as the esters or amides of para-aminobenzoic acid; derivatives of salicylic acid; derivatives of benzophenone; derivatives of dibenzoyl methane; derivatives of diphenyl acrylates; derivatives of benzofurans; UV filter polymers containing one or more silico-organic residues; esters of cinnamic acid; derivatives of camphor; derivatives of trianilino-s-triazine; the ethylic ester urocanic acid; benzotriazoles; derivatives of hydroxy phenyl triazine; bis-resorcinol-dialkyl amino triazine; and mixtures thereof.

The liposoluble (or lipophilic) organic UV filter according to the invention can be chosen from octyl salicylate; 4-tert-butyl-4'-methoxy dibenzoyl methane; octocrylene; 4-methoxy cinnamate; 2-ethylhexyl [2-ethylhexyl 4-methoxycinnamate]; and 2-(2H-benzotriazol-2-yl)-4-methyl-6-[2-methyl-3-[1,3,3,3-tetramethyl-1-[(trimethyl silyl)oxy] disiloxanyl]propynyl] phenol.

Other UV filters particularly preferred for use herein are derivatives of benzophenones such as 2-hydroxy-4-methoxy benzophenone-5-sulfonic acid, 2-hydroxy-4-methoxy benzophenone, derivatives of benzalmalonates such as poly dimethyl/methyl (3(4-(2,2-bis-ethoxy carbonyl vinyl)-phenoxy)-propenyl) siloxane, derivatives of benzylidene camphor such as b-b'camphosulfonic [1-4 divinylbenzene] acid and derivatives of benzimidazole such as 2-phenyl-benzimidazol-5-sulfonic acid.

Water-insoluble UV filters include various mineral oxides. The mineral oxides may be selected from among titanium oxides, zinc oxides, and cerium oxides. The mineral oxides can be used in the form of ultrafine nanoparticles.

Preferred UV filters include Escalol HP-610 (dimethylpabamido propyl laurdimonium tosylate and propylene glycol stearate) and Crodasorb HP (polyquaternium 59).

The antioxidants or antiradical agents can be selected from phenols such as BHA (tert-butyl-4-hydroxy anisole), BHT (2,6-di-tert-butyl-p-cresol), TBHQ (tert-butyl hydroquinone), polyphenols such as proanthocyanodic oligomers, flavonoids, hindered amines such as tetra amino piperidine, erythorbic acid, polyamines such as spermine, cysteine, glutathione, superoxide dismutase, and lactoferrin.

The vitamins can be selected from ascorbic acid (vitamin C), vitamin E, vitamin E acetate, vitamin E phosphate, B vitamins such as B3 and B5, vitamin PP, vitamin A, and derivatives thereof. The provitamins can be selected from panthenol and retinol.

The protecting agent can be present in an amount 0.001% to 20% by weight, preferably from 0.01% to 10% by weight, and more preferably 0.1 to 5% by weight of the total weight of the final composition.

The composition of the invention can contain a fixing agent.

The fixing agent can be an anionic polymer chosen from polymers containing carboxylic units derived from unsaturated carboxylic mono- or polyacids of the formula:

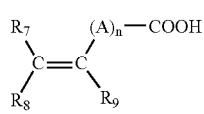

(III)

in which n is a whole number from 0 to 10, $A_1$ denotes a methylene group, optionally bonded to the carbon atom of the unsaturated group or to a neighboring methylene group when n is greater than 1 by means of a heteroatom like oxygen or sulfur, $R_7$ denotes a hydrogen atom, a phenyl or benzyl group, $R_8$ denotes a hydrogen atom, a lower alkyl or carboxyl group, $R_9$ denotes a hydrogen atom, a lower alkyl group, a —$CH_2$—COOH, phenyl or benzyl group and polymers containing units derived from sulfonic acid like vinylsulfonic, styrenesulfonic, acrylamidoalkylsulfonic units.

The fixing agent can be an amphoteric polymer chosen from the polymer containing recurring units derived from:

a) at least one monomer chosen from acrylamides or methacrylamides substituted on the nitrogen with an alkyl radical, b) at least one acid copolymer containing one or more reactive carboxyl groups, and c) at least one basic comonomer, such as esters with primary, secondary, tertiary, and quaternary amino substituents of acrylic and methacrylic acids and the product of quaternization of dimethylaminoethyl methacrylate with dimethyl or diethyl sulfate.

The fixing agent can be a nonionic polymer chosen from polyalkyloxazolines; vinyl acetate homopolymers; vinyl acetate and acrylic ester copolymers; vinyl acetate and ethylene copolymers; vinyl acetate and maleic ester copolymers; polyethylene and maleic anhydride copolymers; homopolymers of alkyl acrylates; homopolymers of alkyl methacrylates; copolymers of acrylic esters; copolymers of alkyl acrylates and alkyl methacrylates; copolymers of acrylonitrile and a nonionic monomer chosen from among butadiene and alkyl (meth)acrylates; copolymers of alkyl acrylate and urethane; and polyamides.

The fixing polymer can be a functionalized or unfunctionalized, silicone or non-silicone polyurethane.

The fixing polymer can be a polymer of the grafted silicone type containing a polysiloxane portion and a portion consisting of a nonsilicone organic chain, with one of the two portions forming the main chain of the polymer, and with the other being grafted onto said main chain.

The fixing agent can be present in the composition in a relative weight concentration between 0.1 and 10%, preferably 0.5 and 5%.

The composition of the invention can contain an oxidizing agent. The oxidizing agent can be chosen from the group of hydrogen peroxide, urea peroxide, alkali metal bromates, ferricyanides, persalts, and redox enzymes, optionally with their respective donor or cofactor. In a particularly preferred embodiment, the oxidizing agent is hydrogen peroxide. The oxidizing agent can be a solution of oxygenated water whose titer varies from 1 to 40 volumes.

The composition of the invention can contain at least one reducing agent in amounts from 0.01 to 30 wt %, preferably 0.05 to 20 wt % of the total weight of the composition. The reducing agents useful in the practice of this invention can be selected from thiols, like cysteine, thioglycolic acid, thiolactic acid, their salts and esters, cysteamine, and its salts or sulfites. In the case of compositions intended for bleaching, ascorbic acid, its salts and its esters, erythorbic acid, its salts and its esters, and sulfinates, like sodium hydroxymethanesulfinate can be used.

The composition of the invention can contain a dye selected from the group consisting of neutral acid or cationic nitrobenzene dyes, neutral acid or cationic azo dyes, quinone dyes, neutral, acid or cationic anthraquinone dyes, azine dyes, triarylmethane dyes, indoamine dyes and natural dyes. The dye or dyes can be present in a concentration from 0.001 to 20% and preferably 0.005 to 10 wt % based on the total weight of the composition.

The composition of the invention can contain at least one amphoteric polymer or a cationic polymer different from the cationic poly(vinyllactam) defined above. Suitable cationic polymers include a poly(quaternary ammonium) consisting of recurrent units corresponding to the following formulae (W) and (U):

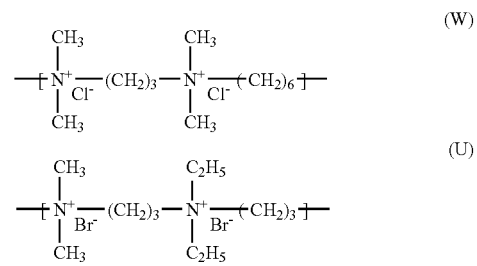

Suitable amphoteric polymers include a copolymer containing at least one acrylic acid and a dimethyldiallyammonium salt as a monomer. The cationic or amphoteric polymer or polymers can be present in an amount of 0.01 to 10%, preferably 0.05 to 5%, and more preferably 0.1 to 3% by weight of the total weight of the composition.

In addition, the compositions according to the invention advantageously include at least one surfactant, which can be present in an amount of 0.1% and 60% preferably 1% and 40%, and more preferably 5% and 30% by weight based on the total weight of the composition. The surfactant may be chosen from among anionic, amphoteric, or non-ionic surfactants, or mixtures of them known to be useful in personal care compositions.

The composition of the invention can contain one or more additional cosmetically acceptable additives chosen from conditioning agents, protecting agents, such as, for example, hydrosoluble, liposoluble and water-insoluble UV filters, antiradical agents, antioxidants, vitamins and pro-vitamins, fixing agents, oxidizing agents, reducing agents, dyes, cleansing agents, anionic, cationic, nonionic and amphoteric surfactants, thickeners, perfumes, pearlizing agents, stabilizers, pH adjusters, filters, preservatives, hydroxy acids, cationic and nonionic polyether associative polyurethanes, polymers other than the cationic polymer described herein, vegetable oils, mineral oils, synthetic oils, polyols such as glycols and glycerol, silicones, aliphatic alcohols, colorants, bleaching agents, highlighting agents and sequestrants. These additives are present in the composition according to the invention in proportions that may range from 0 to 20% by weight in relation to the total weight of the composition. The precise amount of each additive may be easily determined by an expert in the field according to its nature and its function.

Additional thickeners or viscosity increasing agents may be included in the composition of the invention, such as:
Acetamide MEA
Acrylamide/Ethalkonium Chloride Acrylate Copolymer
Acrylamide/Ethyltrimonium Chloride Acrylate/Ethalkonium Chloride Acrylate
Copolymer
Acrylamides Copolymer
Acrylamide/Sodium Acrylate Copolymer
Acrylamide/Sodium Acryloyldimethyltaurate Copolymer
Acrylates/Acetoacetoxyethyl Methacrylate Copolymer
Acrylates/Beheneth-25 Methacrylate Copolymer
Acrylates/C10–30 Alkyl Acrylate Crosspolymer
Acrylates/Ceteth-20 Itaconate Copolymer
Acrylates/Ceteth-20 Methacrylate Copolymer
Acrylates/Laureth-25 Methacrylate Copolymer
Acrylates/Palmeth-25 Acrylate Copolymer
Acrylates/Palmeth-25 Itaconate Copolymer
Acrylates/Steareth-50 Acrylate Copolymer
Acrylates/Steareth-20 Itaconate Copolymer
Acrylates/Steareth-20 Methacrylate Copolymer
Acrylates/Stearyl Methacrylate Copolymer
Acrylates/Vinyl Isodecanoate Crosspolymer
Acrylic Acid/Acrylonitrogens Copolymer
Adipic Acid/Methyl DEA Crosspolymer
Agar
Agarose
Alcaligenes Polysaccharides
Algin
Alginic Acid
Almondamide DEA
Almondamidopropyl Betaine
Aluminum/Magnesium Hydroxide Stearate
Ammonium Acrylates/Acrylonitrogens Copolymer
Ammonium Acrylates Copolymer
Ammonium Acryloyldimethyltaurate/Vinyl Formamide Copolymer
Ammonium Acryloyldimethyltaurate/VP Copolymer
Ammonium Alginate
Ammonium Chloride
Ammonium Polyacryloyidimethyl Taurate
Ammonium Sulfate
Amylopectin
Apricotamide DEA
Apricotamidopropyl Betaine
Arachidyl Alcohol
Arachidyl Glycol
*Arachis Hypogaea* (Peanut) Flour
Ascorbyl Methylsilanol Pectinate
*Astragalus* Gummifer Gum
Attapulgite
*Avena Sativa* (Oat) Kernel Flour
Avocadamide DEA
Avocadamidopropyl Betaine
Azelamide MEA
Babassuamide DEA
Babassuamide MEA
Babassuamidopropyl Betaine
Behenamide DEA
Behenamide MEA
Behenamidopropyl Betaine
Behenyl Betaine
Bentonite
Butoxy Chitosan
*Caesalpinia Spinosa* Gum
Calcium Alginate
Calcium Carboxymethyl Cellulose
Calcium Carrageenan
Calcium Chloride
Calcium Potassium Carbomer
Calcium Starch Octenylsuccinate
C20–40 Alkyl Stearate
Canolamidopropyl Betaine
Capramide DEA
Capryl/Capramidopropyl Betaine
Carbomer
Carboxybutyl Chitosan
Carboxymethyl Cellulose Acetate Butyrate
Carboxymethyl Chitin
Carboxymethyl Chitosan
Carboxymethyl Dextran
Carboxymethyl Hydroxyethylcellulose
Carboxymethyl Hydroxypropyl Guar
Carnitine
Cellulose Acetate Propionate Carboxylate
Cellulose Gum
*Ceratonia Siliqua* Gum
Cetearyl Alcohol
Cetyl Alcohol
Cetyl Babassuate
Cetyl Betaine
Cetyl Glycol
Cetyl Hydroxyethylcellulose
Chimyl Alcohol
Cholesterol/HDI/Pullulan Copolymer
Cholesteryl Hexyl Dicarbamate Pullulan
*Citrus Aurantium Dulcis* (Orange) Peel Extract
Cocamide DEA
Cocamide MEA
Cocamide MIPA
Cocamidoethyl Betaine
Cocamidopropyl Betaine
Cocamidopropyl Hydroxysultaine
Coco-Betaine
Coco-Hydroxysultaine
Coconut Alcohol
Coco/Oleamidopropyl Betaine
Coco-Sultaine
Cocoyl Sarcosinamide DEA
Cornamide/Cocamide DEA
Cornamide DEA
Croscarmellose
Crosslinked *Bacillus*/Glucose/Sodium Glutamate Ferment
*Cyamopsis Tetragonoloba* (Guar) Gum
Decyl Alcohol
Decyl Betaine
Dehydroxanthan Gum
Dextrin Dibenzylidene Sorbitol
Diethanolaminooleamide DEA
Diglycol/CHDM/Isophthalates/SIP Copolymer
Dihydroabietyl Behenate
Dihydrogenated Tallow Benzylmonium Hectorite
Dihydroxyaluminum Aminoacetate
Dimethicone/PEG-10 Crosspolymer
Dimethicone/PEG-15 Crosspolymer
Dimethicone Propyl PG-Betaine
Dimethylacrylamide/Acrylic Acid/Polystyrene Ethyl Methacrylate Copolymer
Dimethylacrylamide/Sodium Acryloyldimethyltaurate Crosspolymer
Disteareth-100 IPDI
DMAPA Acrylates/Acrylic Acid/Acrylonitrogens Copolymer
Erucamidopropyl Hydroxysultaine
Ethylene/Sodium Acrylate Copolymer
Gelatin
Gellan Gum
Glyceryl Alginate
Glycine Soja (Soybean) Flour
Guar Hydroxypropyltrimonium Chloride
Hectorite
Hyaluronic Acid
Hydrated Silica
Hydrogenated Potato Starch
Hydrogenated Tallow
Hydrogenated Tallowamide DEA
Hydrogenated Tallow Betaine
Hydroxybutyl Methylcellulose
Hydroxyethyl Acrylate/Sodium Acryloyldimethyl Taurate Copolymer
Hydroxyethylcellulose
Hydroxyethyl Chitosan
Hydroxyethyl Ethylcellulose
Hydroxyethyl Stearamide-MIPA
Hydroxylauryl/Hydroxymyristyl Betaine
Hydroxypropylcellulose
Hydroxypropyl Chitosan
Hydroxypropyl Ethylenediamine Carbomer
Hydroxypropyl Guar
Hydroxypropyl Methylcellulose
Hydroxypropyl Methylcellulose Stearoxy Ether
Hydroxypropyl Starch
Hydroxypropyl Starch Phosphate
Hydroxypropyl Xanthan Gum
Hydroxystearamide MEA
Isobutylene/Sodium Maleate Copolymer
Isostearamide DEA
Isostearamide MEA
Isostearamide MIPA
Isostearamidopropyl Betaine
Lactamide MEA
Lanolinamide DEA
Lauramide DEA
Lauramide MEA
Lauramide MIPA
Lauramide/Myristamide DEA
Lauramidopropyl Betaine
Lauramidopropyl Hydroxysultaine
Laurimino Bispropanediol
Lauryl Alcohol
Lauryl Betaine
Lauryl Hydroxysultaine
Lauryl/Myristyl Glycol Hydroxypropyl Ether
Lauryl Sultaine
Lecithinamide DEA
Linoleamide DEA
Linoleamide MEA
Linoleamide MIPA
Lithium Magnesium Silicate
Lithium Magnesium Sodium Silicate
*Macrocystis Pyrifera* (Kelp)
Magnesium Alginate
Magnesium/Aluminum/Hydroxide/Carbonate
Magnesium Aluminum Silicate
Magnesium Silicate
Magnesium Trisilicate
Methoxy PEG-22/Dodecyl Glycol Copolymer
Methylcellulose
Methyl Ethylcellulose
Methyl Hydroxyethylcellulose
Microcrystalline Cellulose
Milkamidopropyl Betaine
Minkamide DEA
Minkamidopropyl Betaine
MIPA-Myristate
Montmorillonite
Moroccan Lava Clay
Myristamide DEA
Myristamide MEA
Myristamide MIPA
Myristamidopropyl Betaine
Myristamidopropyl Hydroxysultaine
Myristyl Alcohol
Myristyl Betaine
Natto Gum
Nonoxynyl Hydroxyethylcellulose
Oatamide MEA
Oatamidopropyl Betaine
Octacosanyl Glycol Isostearate
Octadecene/MA Copolymer
Oleamide DEA
Oleamide MEA
Oleamide MIPA
Oleamidopropyl Betaine
Oleamidopropyl Hydroxysultaine
Oleyl Betaine
Olivamide DEA
Olivamidopropyl Betaine
Oliveamide MEA
Palmamide DEA
Palmamide MEA
Palmamide MIPA
Palmamidopropyl Betaine
Palmitamide DEA
Palmitamide MEA
Palmitamidopropyl Betaine
Palm Kernel Alcohol
Palm Kernelamide DEA
Palm Kernelamide MEA
Palm Kernelamide MIPA
Palm Kernelamidopropyl Betaine
Peanutamide MEA
Peanutamide MIPA
Pectin
PEG-800
PEG-Crosspolymer
PEG-150/Decyl Alcohol/SMDI Copolymer
PEG-175 Diisostearate
PEG-190 Distearate
PEG-15 Glyceryl Tristearate
PEG-140 Glyceryl Tristearate PEG-240/HDI Copolymer Bis-Decyltetradeceth-20 Ether
PEG-100/IPDI Copolymer
PEG-180/Laureth-50/TMMG Copolymer
PEG-10/Lauryl Dimethicone Crosspolymer
PEG-15/Lauryl Dimethicone Crosspolymer
PEG-2M
PEG-5M
PEG-7M
PEG-9M
PEG-14M
PEG-20M
PEG-23M
PEG-25M
PEG-45M
PEG-65M
PEG-90M
PEG-115M
PEG-160M
PEG-180M
PEG-120 Methyl Glucose Trioleate
PEG-180/Octoxynol-40/TMMG Copolymer
PEG-150 Pentaerythrityl Tetrastearate
PEG-4 Rapeseedamide
PEG-150/Stearyl Alcohol/SMDI Copolymer
*Phaseolus Angularis* Seed Powder
Polianthes Tuberosa Extract
Polyacrylate-3
Polyacrylic Acid
Polycyclopentadiene
Polyether-1
Polyethylene/Isopropyl Maleate/MA Copolyol
Polyglyceryl-3 Disiloxane Dimethicone
Polyglyceryl-3 Polydimethylsiloxyethyl Dimethicone
Polymethacrylic Acid
Polyquaternium-52
Polyvinyl Alcohol
Potassium Alginate
Potassium Aluminum Polyacrylate
Potassium Carbomer
Potassium Carrageenan
Potassium Chloride
Potassium Palmate
Potassium Polyacrylate
Potassium Sulfate
Potato Starch Modified
PPG-2 Cocamide
PPG-1 Hydroxyethyl Caprylamide
PPG-2 Hydroxyethyl Cocamide
PPG-2 Hydroxyethyl Coco/Isostearamide
PPG-3 Hydroxyethyl Soyamide
PPG-14 Laureth-60 Hexyl Dicarbamate
PPG-14 Laureth-60 Isophoryl Dicarbamate
PPG-14 Palmeth-60 Hexyl Dicarbamate
Propylene Glycol Alginate
PVP/Decene Copolymer
PVP Montmorillonite
*Pyrus Cydonia* Seed
*Pyrus Malus* (Apple) Fiber
Rhizobian Gum
Ricebranamide DEA
Ricinoleamide DEA
Ricinoleamide MEA
Ricinoleamide MIPA
Ricinoleamidopropyl Betaine
Ricinoleic Acid/Adipic Acid/AEEA Copolymer
*Rosa* Multiflora Flower Wax
*Sclerotium* Gum
Sesamide DEA
Sesamidopropyl Betaine
Sodium Acrylate/Acryloyldimethyl Taurate Copolymer
Sodium Acrylates/Acrolein Copolymer
Sodium Acrylates/Acrylonitrogens Copolymer
Sodium Acrylates Copolymer
Sodium Acrylates Crosspolymer
Sodium Acrylate/Sodium Acrylamidomethylpropane Sulfonate Copolymer
Sodium AcrylatesNinyl Isodecanoate Crosspolymer
Sodium Acrylate/Vinyl Alcohol Copolymer
Sodium Carbomer
Sodium Carboxymethyl Chitin
Sodium Carboxymethyl Dextran
Sodium Carboxymethyl Beta-Glucan
Sodium Carboxymethyl Starch
Sodium Carrageenan
Sodium Cellulose Sulfate
Sodium Chloride
Sodium Cyclodextrin Sulfate
Sodium Hydroxypropyl Starch Phosphate
Sodium Isooctylene/MA Copolymer
Sodium Magnesium Fluorosilicate
Sodium Oleate
Sodium Palmitate
Sodium Palm Kernelate
Sodium Polyacrylate
Sodium Polyacrylate Starch
Sodium Polyacryloyldimethyl Taurate
Sodium Polygamma-Glutamate
Sodium Polymethacrylate
Sodium Polystyrene Sulfonate
Sodium Silicoaluminate
Sodium Starch Octenylsuccinate
Sodium Stearate
Sodium Stearoxy PG-Hydroxyethylcellulose Sulfonate
Sodium Styrene/Acrylates Copolymer
Sodium Sulfate
Sodium Tallowate
Sodium Tauride Acrylates/Acrylic Acid/Acrylonitrogens Copolymer
Sodium Tocopheryl Phosphate
*Solanum Tuberosum* (Potato) Starch
Soyamide DEA
Soyamidopropyl Betaine
Starch/Acrylates/Acrylamide Copolymer
Starch Hydroxypropyltrimonium Chloride
Stearamide AMP
Stearamide DEA
Stearamide DEA-Distearate
Stearamide DIBA-Stearate
Stearamide MEA
Stearamide MEA-Stearate
Stearamide MIPA
Stearamidopropyl Betaine
Steareth-60 Cetyl Ether
Steareth-100/PEG-136/HDI Copolymer
Stearyl Alcohol
Stearyl Betaine
*Sterculia Urens* Gum
Synthetic Fluorphlogopite
Tallamide DEA
Tallow Alcohol
Tallowamide DEA
Tallowamide MEA
Tallowamidopropyl Betaine
Tallowamidopropyl Hydroxysultaine Tallowamine Oxide
Tallow Betaine
Tallow Dihydroxyethyl Betaine
*Tamarindus Indica* Seed Gum
Tapioca Starch
TEA-Alginate
TEA-Carbomer
TEA-Hydrochloride
Trideceth-2 Carboxamide MEA
Tridecyl Alcohol
Triethylene Glycol Dibenzoate
Trimethyl Pentanol Hydroxyethyl Ether
*Triticum Vulgare* (Wheat) Germ Powder
*Triticum Vulgare* (Wheat) Kernel Flour
*Triticum Vulgare* (Wheat) Starch
Tromethamine Acrylates/Acrylonitrogens Copolymer
Tromethamine Magnesium Aluminum Silicate
Undecyl Alcohol
Undecylenamide DEA
Undecylenamide MEA
Undecylenamidopropyl Betaine
Welan Gum
Wheat Germamide DEA
Wheat Germamidopropyl Betaine
Xanthan Gum
Yeast Beta-Glucan
Yeast Polysaccharides and
*Zea Mays* (Corn) Starch.

Preferred thickeners or viscosity increasing agents include Carbomer, Aculyn and Stabileze, e.g. crosslinked acrylic acid, crosslinked poly(methylvinyl ether/maleic anhydride) copolymer, acrylamides, carboxymethyl cellulose and the like.

The compositions according to the invention may be used to wash and treat keratinous material such as hair, skin, eyelashes, eyebrows, fingernails, lips, and hairy skin.

The compositions according to the invention can be detergent compositions such as shampoos, bath gels, and bubble baths. In this mode, the compositions will comprise a generally aqueous washing base. The surfactant or surfactants that form the washing base may be chosen alone or in blends, from known anionic, amphoteric, or non-ionic surfactants. The quantity and quality of the washing base must be sufficient to impart a satisfactory foaming and/or detergent value to the final composition. The washing base can be from 4% to 50% by weight, preferably from 6% to 35% by weight, and even more preferentially from 8% to 25% by weight of the total weight of the final composition.

The pH of the composition applied to the keratinous material is generally between 2 and 12. It is preferably between 3 and 8, and may be adjusted to the desired value by means of acidifying or alkalinizing agents that are well-known in the state of the art in compositions applied to keratinous materials. Thus, the composition of the invention can contain at least one alkalizing or acidifying agent in amounts from 0.01 to 30 wt % of the total weight of the composition.

The alkalizing agent can be chosen from ammonia, alkali carbonates, alkanolamines, like mono-, di- and triethanolamines, as well as their derivatives, hydroxyalkylamines and ethoxylated and/or propoxylated ethylenediamines, sodium or potassium hydroxides and compounds of the following formula (XIX):

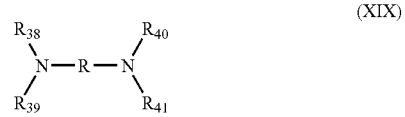

in which R is a propylene residue optionally substituted with an hydroxyl group or a $C_1$–$C_4$ alkyl radical; $R_{38}$, $R_{39}$, $R_{40}$ and $R_{41}$, identical or different, represent a hydrogen atom, a $C_1$–$C_4$ alkyl radical or $C_1$–$C_4$ hydroxyalkyl radical.

The acidifying agent can be chosen from mineral or organic acids, like hydrochloric acid, orthophosphoric acid, carboxylic acids like tartaric acid, citric acid, or lactic acid, or sulfonic acids and the like.

The physiological and cosmetically acceptable medium may consist exclusively of water, a cosmetically acceptable solvent, or a blend of water and a cosmetically acceptable solvent, such as a lower alcohol composed of $C_1$ to $C_4$, such as ethanol, isopropanol, t-butanol, n-butanol, alkylene glycols such as propylene glycol, and glycol ethers. However, the compositions of the invention can be anhydrous.

Generally the present cosmetic compositions are prepared by simple mixing procedures well known in the art.

The invention also has as its object a process for treating keratinous material including the skin or hair, characterized in that it consists of applying to skin or keratinous materials a cosmetic composition as described above, and then eventually rinsing it with water. Accordingly, the process according to the invention makes it possible to maintain the hairstyle, treatment, care, washing, or make-up removal of the skin, the hair, and any other keratinous material.

The compositions according to the invention may also take the form of after-shampoo compositions, to be rinsed off or not, for permanents, straightening, waving, dyeing, or bleaching, or the form of rinse compositions to be applied before or after dyeing, bleaching, permanents, straightening, relaxing, waving or even between the two stages of a permanent or straightening process.

The compositions of the invention may also take the form of skin-washing compositions, and particularly in the form of solutions or gels for the bath or shower, or of make-up removal products.

The compositions of the invention may also be in the form of aqueous or hydro-alcoholic solutions for skin and/or hair care.

The compositions of this invention have demonstrated thermal protection from heat styling tools, more specifically curling or straightening irons. In this application, the cationic polymer provides a continuous film on hair that does not degrade nor whiten upon regular exposure to curling irons at temperatures up to 152° C. Protection is observed via tryptophan measurements and perceived by consumer in combing force reduction.

The compositions described herein are useful in products for personal care, including, but mot limited to, gels, lotions, glazes, glues, mousses, sprays, fixatives, shampoos, conditioners, 2n1 shampoos, temporary hair dyes, semi-permanent hair dyes, permanent hair dyes, straighteners, permanent waves, relaxers, creams, putties, waxes, pomades, moisturizers, mascaras, lip balms and foam enhancers.

While the invention has been described with particular reference to certain embodiments thereof, it will be understood that changes and modifications may be made which are within the skill of the art. Accordingly, it is intended to be bound only by the following claims, in which:

What is claimed is:

1. A rheology modifier/hair styling resin consisting of a crosslinked, linear poly(vinyl amide/polymerizable carboxylic acid) copolymer having a composition, by weight, of 25–75% of a vinyl amide monomer selected from vinyl pyrrolidone. vinyl caprolactam, N-vinyl formamide, N-vinyl-acetamide, N-vinyl-N-methylacetamide and mixtures thereof, and 25–75% of a polymerizable carboxylic acid monomer selected from (meth)acrylic acid, crotonic acid, itaconic acid, maleic acid and mixtures thereof, and a crosslinker in an amount of 0.5–2%. based on weight of total monomers, which is characterized by an aqueous solution having a viscosity of 55,000 cps at a pH of 9 (Brookfield RVT, T-bar C@ 10 RPM, 60 sec., 1% resin solids in water).

2. A rheology modifier/hair styling resin according to claim 1 wherein said vinyl amide is vinyl pyrrolidone.

3. A rheology modifier/hair styling resin according to claim 1 wherein said polymerizable carboxylic acid is acrylic acid.

4. A rheology modifier/hair styling resin according to claim 1 wherein said crosslinker has at least two free radical polymerizable groups in the molecule.

5. A rheology modifier/hair styling resin according to claim 4 wherein said crosslinker is selected from pentaerythritol triallylether, pentaerythritol triacrylate, pentaerythritol tetraacrylate and methylene bisacrylamide.

6. A process of making the rheology modifier/hair styling resin of claim 1 which consists of precipitation polymerizing, by wt., 5–50% of a reaction mixture of 25–75% of a vinyl amide and 25–75% of a polymerizable carboxylic acid, and 0.5–2% of a crosslinker, based on total monomers, in 50–95% of a non-polar removable organic solvent, in the presence of 0.1–5% of a free radical initiator, based on total weight of monomers, and removing the solvent, to provide the resin in powder form.

7. A process according to claim 6 wherein said reaction mixture consists of 10–25% of said monomers and 75–90% of said solvent.

8. A hair care composition including the rheology modifier/hair styling resin of claim 1.

9. A hair care composition according to claim 8 including 0.1–20% by wt. of said resin.

10. A hair care composition according to claim 8 which exhibits a curl retention of 80% to 100% over a 4-hour period at 90% RH and 80° F.

11. A hair care composition according to claim 10 wherein said retention is about 90%.

12. A personal care composition including the resin of claim 1.

13. A personal care composition according to claim 12 which is a skin care formulation.

14. A personal care composition according to claim 13 which is an absorbent composition.

15. A personal care composition according to claim 12 which includes a thickener.

16. A personal care composition according to claim 15 wherein said thickener is a crosslinked polyacrylic acid or its copolymer.

17. A personal care composition according to claim 15 wherein said thickener is crosslinked polymethylvinyl ether/maleic anhydride copolymer.

18. An aqueous hair care composition according to claim 8 having a yield stress value of 10 to 100,000 dynes/cm$^2$.

19. A composition according to claim 18 wherein said value is 100 to 10,000 dynes/cm$^2$.

20. A hair care composition including the rheology modifier of claim 1 which is a hair fixative, a styling gel, a crème, a mousse, or a spray.

21. A hair care composition according to claim 9 which includes 0.2–10% by wt. of said resin.

22. A hair care composition according to claim 21 which includes 0.5–5% by wt. of said resin.

* * * * *